United States Patent [19]
Butler et al.

[11] Patent Number: 5,133,731
[45] Date of Patent: Jul. 28, 1992

[54] EMBOLUS SUPPLY SYSTEM AND METHOD

[75] Inventors: James R. Butler, Ingleside, Ill.;
William C. McCoy, Zionsville, Ind.;
Arnold Miller, Chestnut Hill, Mass.

[73] Assignee: Catheter Research, Inc., Indianapolis, Ind.

[21] Appl. No.: 612,107

[22] Filed: Nov. 9, 1990

[51] Int. Cl.$^5$ .............................................. A61B 17/00
[52] U.S. Cl. .................................. 606/191; 606/198; 606/195
[58] Field of Search ............... 606/200, 195, 198, 151, 606/108, 191; 604/104; 128/831, 843

[56] References Cited

U.S. PATENT DOCUMENTS

| | | |
|---|---|---|
| 1,694,246 | 12/1928 | Boyne . |
| 2,269,963 | 1/1942 | Wappler . |
| 3,833,003 | 9/1974 | Taricco . |
| 4,282,875 | 8/1981 | Serbinenko et al. . |
| 4,445,896 | 5/1984 | Gianturco . |
| 4,471,779 | 9/1984 | Antoshkiw et al. . |
| 4,494,531 | 1/1985 | Gianturco . |
| 4,512,342 | 4/1985 | Zaneveld et al. . |
| 4,543,090 | 9/1985 | McCoy . |
| 4,545,367 | 10/1985 | Tucci . |
| 4,601,705 | 7/1986 | McCoy . |
| 4,655,746 | 4/1987 | Daniels et al. . |
| 4,662,885 | 5/1987 | DiPisa, Jr. . |
| 4,686,962 | 8/1987 | Haber . |
| 4,688,553 | 8/1987 | Metals . |
| 4,708,718 | 11/1987 | Daniels . |
| 4,732,152 | 3/1988 | Wallsten et al. . |
| 4,739,768 | 4/1988 | Engelson . |
| 4,744,364 | 5/1988 | Kensey . |
| 4,758,222 | 7/1988 | McCoy . |
| 4,800,882 | 1/1989 | Gianturco . |
| 4,813,934 | 3/1989 | Engelson et al. . |
| 4,832,047 | 5/1989 | Sepetka et al. . |
| 4,884,579 | 12/1989 | Engelson . |
| 4,944,727 | 7/1990 | McCoy . |
| 4,994,069 | 2/1991 | Ritchart et al. . |

FOREIGN PATENT DOCUMENTS 223065 6/1985 Fed. Rep. of Germany .

OTHER PUBLICATIONS

Perry, Stanton B. et al, "Coil Embolization to Occlude Aortopulmonary Collateral Vessels and Shunts in Patients with Congenital Heart Disease", J. Am. Coll. Cardiol., vol. 13, Jan. 1989, pp. 100–108.

Hawkins, Jeffrey et al, "Retrievable Gianturco-Coil Introducer", Radiology, vol. 158, Jan. 1986, pp. 262–264.

Fuhrman, Bradley P. et al, "Coil Embolization of Congenital Thoracic Vascular Anomalies in Infants and Children", Therapy and Prevention-Vascular Anomalies, vol. 70, No. 2, Aug. 1984, pp. 285–289.

Berkman, William A. et al, "Varicoceles: A Coaxial Coil Occlusion System", Radiology, vol. 161, No. 1, Apr. 1984, pp. 73–77.

Ralston, Matthew D. et al, "Evaluation of Embolization Distal to Arterial Occlusion by Transcatheter Electrocoagulation (TCEC) and Gianturco Coils", Investigative Radiology, vol. 18, Mar.–Apr. 1983, pp. 171–176.

Chuang, Vincent P. et al, "Complications of Coil Embolization: Prevention and Management", AJR 137, Oct. 1981, pp. 809–813.

(List continued on next page.)

Primary Examiner—Michael H. Thaler
Attorney, Agent, or Firm—Barnes & Thornburg

[57] ABSTRACT

An apparatus and method is provided for dispensing coil emboli one at a time in a controlled and reliable manner during surgery to embolize several blood vessels or the like in a body. The apparatus includes a magazine that is movable within a dispenser housing to position each of the embolus cartridges contained in the magazine one at a time at a dispensing station on command. A stream of pressurized fluid is injected or a guide wire is inserted into the embolus cartridge held in the dispensing station to dislodge an embolus contained therein and discharge it into an embolus-delivery catheter coupled to the dispenser housing. Afterwards, the magazine is moved within the dispenser housing to remove the just-emptied embolus cartridge from the dispensing station and load a fresh embolus cartridge into the dispensing station.

48 Claims, 6 Drawing Sheets

OTHER PUBLICATIONS

Szarnicki, Robert et al, "Wire Coil Embolization of Systemic-Pulmonary Artery Collaterals Following Surgical Correction of Pulmonary Artresia", J. Thorac. Cardiovasc. Surg., vol. 81, No. 1, Jan. 1981, pp. 124–126.

Gianturco, C. et al, "Mechanical Devices for Arterial Occlusion", vol. 124, No. 3, Jul. 1975, pp. 428–435.

Anderson, James H. et al, "'Mini' Gianturco Stainless Steel Coils for Transcatheter Vascular Occulsion", Diagnostic Radiology, vol. 132, Aug. 1979, pp. 301–303.

Chuang, Vincent P. et al, "A New Improved Coil for Tapered-Tip Catheter for Arterial Occlusion", Radiology, vol. 135, May 1980, pp. 507–509.

Thompson, James N. et al, "Embolization Techniques in Vascular Tumors of the Head and Neck", Head & Neck Surgery, vol. 2, Sep.–Oct. 1979, pp. 25–34.

LeMaitre, George D. et al, "In Situ Grafting Made Easy", Arch. Surg., vol. 123, Jan. 1989, pp. 101–103.

Leather, Robert P. et al, "Instrumental Evolution of the Valve Incision Method of In Situ Saphenous Vein Bypass", J. Vasc. Surg., vol. 1, 1984, pp. 113–123.

Leather, Robert P. et al, "In-Situ Saphenous Vein Arterial Bypass for the Treatment of Limb Ischemia", Advances in Surgery, vol. 19, 1986, pp. 175–219.

Pigott, John P. et al, "Angioscope-Assisted Occlusion of Venous Tributaries with Prolamine in situ Femoropopliteal Bypass: Preliminary Results of Canine Experiments", Journal of Vascular Surgery, vol. 9, No. 5, pp. 704–709.

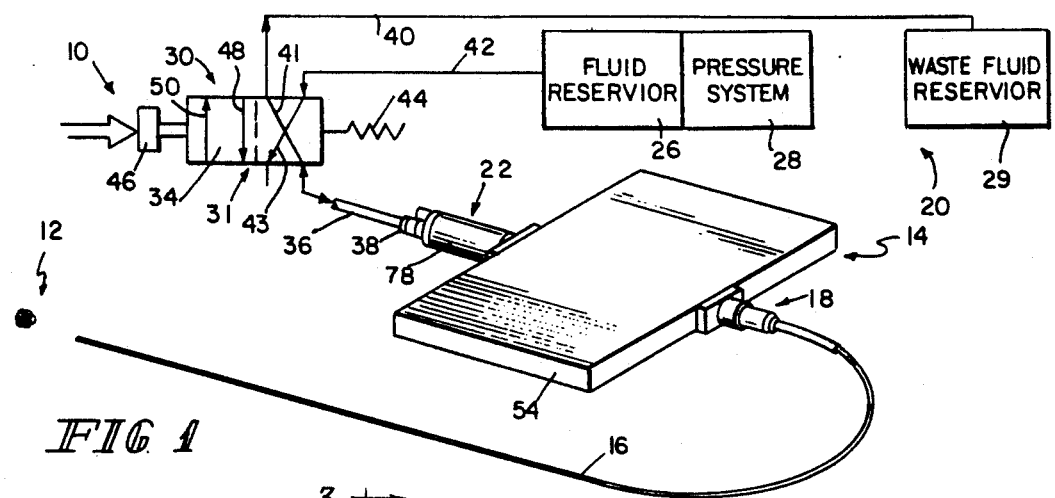
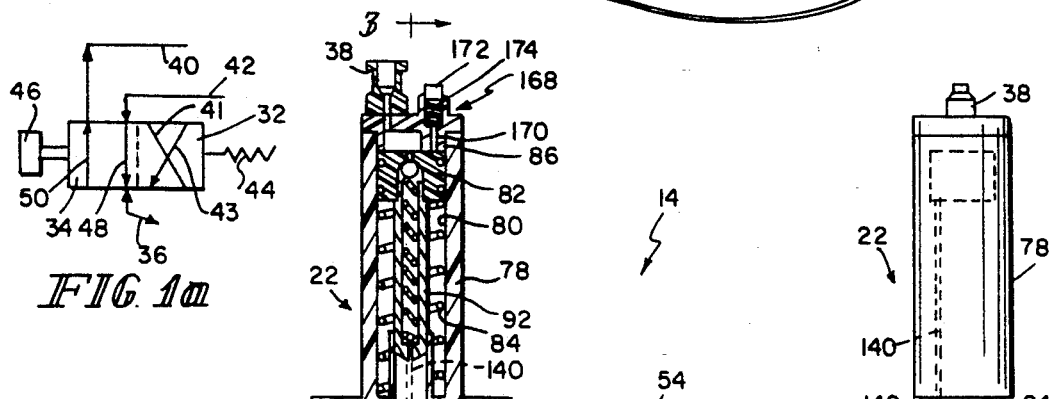
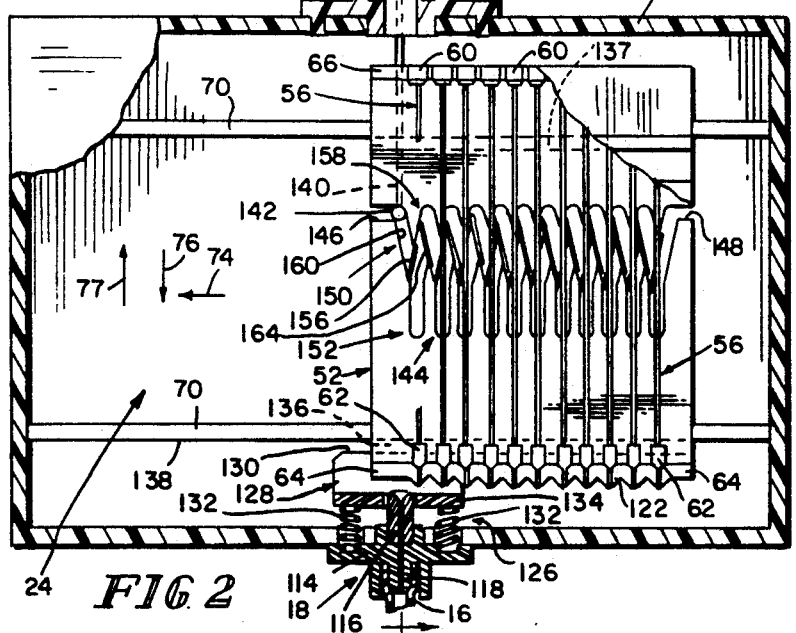
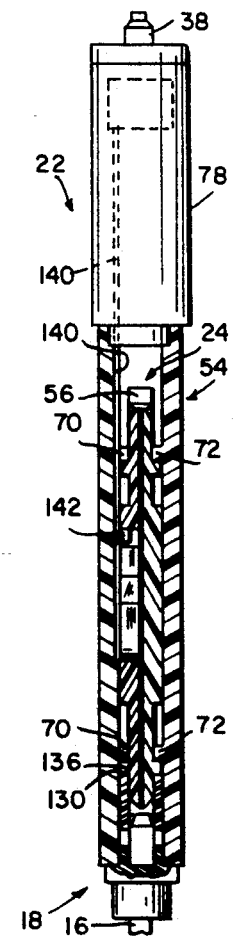
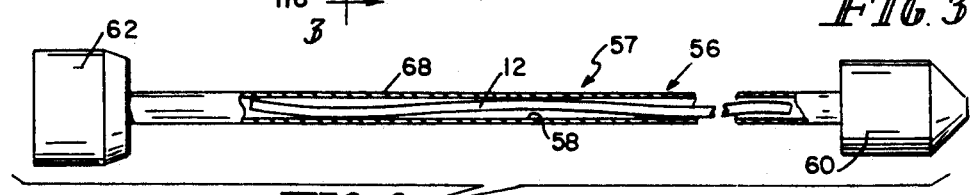

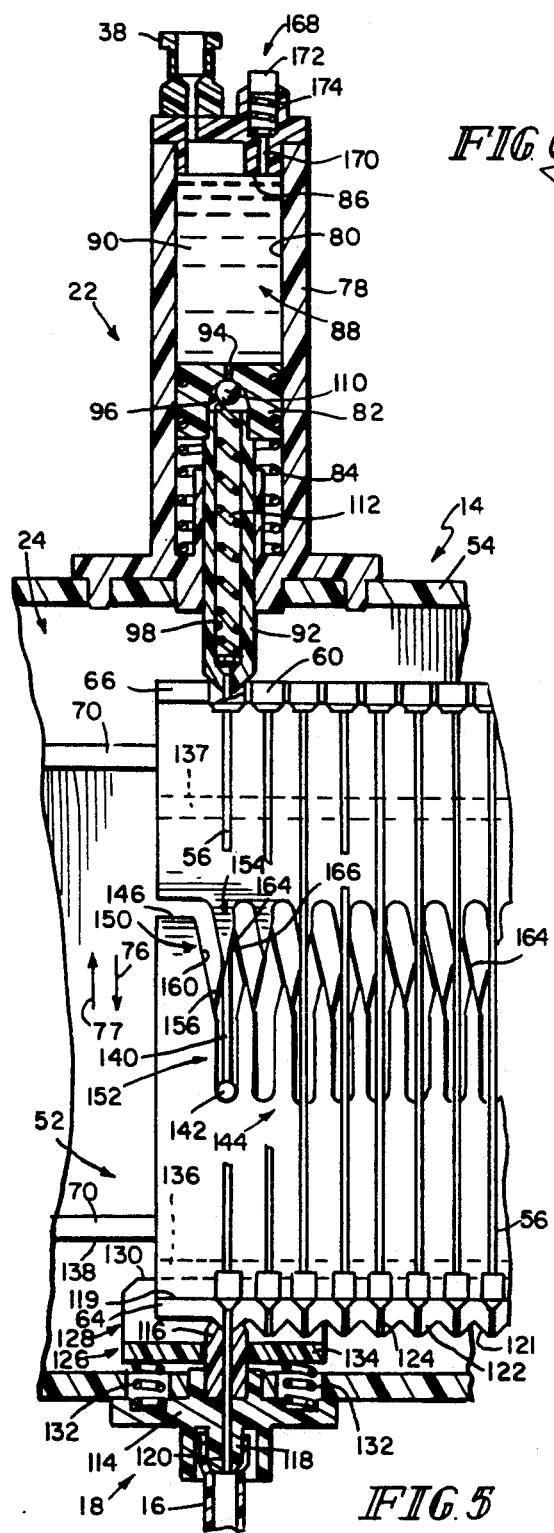
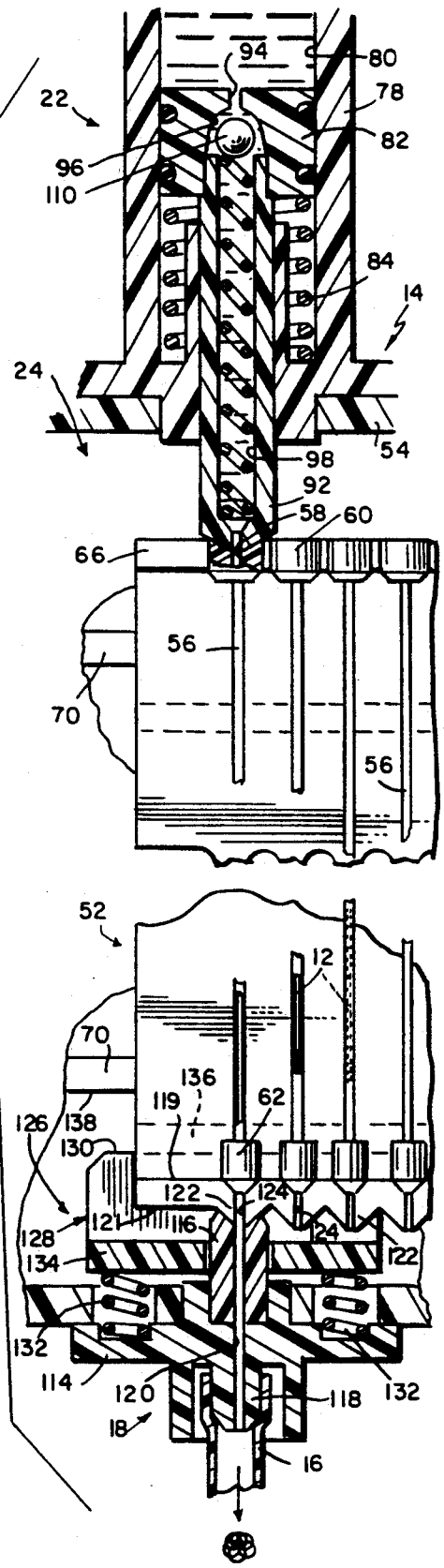
FIG. 5
FIG. 6

5,133,731

EMBOLUS SUPPLY SYSTEM AND METHOD

BACKGROUND AND SUMMARY OF THE INVENTION

This invention relates to a vessel occlusion system, and particularly to a system for supplying an embolus to a catheter or the like for delivery into a vessel situated in a body to occlude or close the vessel. More particularly, this invention relates to an apparatus and method for selecting an embolus and moving it through an introducer catheter inserted through a venotomy into a body to reach a destination in a blood vessel or the like and occlude the vessel during a surgical or percutaneous interventional vascular procedure.

Embolization is a procedure used by surgeons and vascular interventionalists (probably radiologists and cardiologists) to block fluid flow through a blood vessel or organ. Typically, a mass of material called an embolus is inserted into a body using a catheter and lodged in a blood vessel or organ to Provide an obstruction therein. Lodging an embolus in a blood vessel obstructs blood flow through the vessel and causes a thrombus or blood clot to develop in the vessel. The thrombus remains attached to the embolus and blood vessel wall at its place of origin to plug the vessel and obstruct blood or other fluid flow therethrough.

Embolization is used, for example, for therapeutic purposes to reduce blood loss during hemorrhage or treatment of unresectable lesions or to permit preoperative control of blood flow. Embolization of feeding vessels is known to reduce bleeding during surgery. For example, it is used in surgery prior to resection of vascular tumors.

Many types of emboli are known. For example, coils made of spring wire, sponges made of absorbable gelatin or other chemical cross-linking means such as cyanoacrylate or the like, detachable balloons, umbrella-like devices, and other types of plugs are used to embolize a vessel. Any device which has thrombotic properties when placed in a vessel having a proper internal diameter and does not cause significant foreign body reaction can be used to embolize a vessel to occlude the vessel totally or partially.

A guide wire can be used to load an embolus into an introducer catheter or to discharge an embolus from its place in an introducer catheter into a vessel or both. A guide wire sized to pass through the lumen of the introducer catheter can be used to move an embolus into and out of an introducer catheter as long as the surgeon has the necessary skill and expertise.

According to the present invention, an apparatus is provided for supplying an embolus to a delivery tube such as a catheter. The apparatus includes a magazine containing a plurality of emboli to be discharged one at a time into the delivery tube. The magazine is movable relative to the delivery tube to place one of the emboli stored in the magazine in a position opposite the mouth of the delivery tube. A discharge means is used to discharge the selected embolus from the magazine into the delivery tube.

Advantageously, the present invention provides an apparatus and method for selectively discharging a single embolus from a magazine containing many emboli and hydraulically delivering the discharged embolus into a catheter already inserted into a patient's vein or artery. In one embodiment, hydraulic means is used to discharge the embolus from the magazine to a destination and, in another embodiment, a mechanical means such as a guide wire is used instead of the hydraulic means to discharge the embolus. During vascular surgery, the embolus is moved either hydraulically or mechanically through the catheter and is deposited in a blood vessel connected to the vein or artery upon exiting the catheter.

The apparatus is particularly well-suited for use during endoluminal vein preparation for in-situ bypass. This is a surgical procedure designed to reconfigure the vein to function as an artery so that the vein can be surgically adapted to replace a naturally occluded, malfunctioning artery in a leg or other portion of a body. Each embolus discharged from the magazine is delivered to a blood vessel branching out from the vein and deposited therein to help occlude the blood vessel. The apparatus is also well-suited for use in varicose vein surgery and occluding the smaller branches of an artery exposed during surgery, such as during aneurysm repair.

In preferred embodiments, the magazine contains a plurality of separate embolus cartridges arranged side-by-side in a series. Each embolus cartridge holds a single embolus and is formed to include a through passageway containing the embolus. The magazine is movable inside a hollow housing to align each cartridge in the series one at a time in an embolus-discharging position or station located within the housing. The hollow housing includes an inlet coupled to a fluid supply system and an outlet coupled to the delivery tube. An embolus cartridge aligned in the embolus-discharging position is connected to the housing inlet and outlet to conduct fluid from the fluid supply system to the delivery tube through the passageway in the embolus cartridge containing the embolus.

A stream of pressurized fluid is generated using fluid from the fluid supply system and used to move the magazine inside the housing so that each embolus cartridge in the series is aligned one at a time in sequence in the embolus-discharging position within the housing. Illustratively, the apparatus includes a cylinder for receiving the stream of pressurized fluid and a mechanical linkage for advancing the magazine along a guide path within the housing. A piston is movable in the cylinder to operate the mechanical linkage and advance the magazine along the guide path in response to input of pressurized fluid into the cylinder. The mechanical linkage is constructed to ensure that the magazine is moved incrementally within the housing to place each embolus cartridge in sequence in the embolus-discharging position.

Once an embolus cartridge has been moved to the embolus-discharging position in the housing, the stream of pressurized fluid in the cylinder is passed through an aperture formed in the piston and into the embolus-containing passageway in the embolus cartridge. The embolus is discharged by the stream of pressurized fluid from the embolus cartridge and magazine into the delivery tube through the housing outlet to empty the embolus cartridge positioned in the embolus-discharging station. The fluid used to flush the embolus through the delivery tube is water or another biologically compatible fluid such as saline. The fluid-powered mechanical linkage then operates automatically to move the magazine inside the housing to "reload" the embolus supply apparatus so that a just-emptied embolus cartridge is moved out of the embolus-discharging position and a next "loaded" embolus cartridge is moved into the embolus-discharging position and connected to the fluid supply system at the housing inlet and the delivery tube at the housing outlet.

A supply of fluid is provided and a predetermined volume of fluid from the supply is pressurized at a predetermined rate to generate the stream of pressurized fluid. For example, it has been observed that only 0.5-3 cubic centimeters of fluid are needed to deliver an embolus to a target site in a collateral blood vessel.

The embolus is preferably a normally coiled spring that has been straightened to a somewhat linear shape to assume an "uncoiled" configuration for containment in the cylindrical passageway formed in the cartridge. The tendency for the uncoiled spring to reconfigure itself to its coiled configuration causes the spring (embolus) to exert a predetermined force against an interior wall defining the passageway to retain the spring (embolus) temporarily in an initial position within the cartridge passageway. Advantageously, the stream of pressurized fluid is used to apply a predetermined amount of work to the embolus to overcome frictional forces between the embolus and the interior wall of the cartridge passageway to dislodge the embolus from its place in the hollow cartridge so that it can be moved by the stream of pressurized fluid through the catheter to reach its destination in the vessel.

Illustratively, the catheter used to deliver the embolus to the target site is guided through various body passageways to reach the target site by means of a second catheter having a lumen sized to receive the embolus-delivery catheter therein. The second catheter is preferably steerable and aimable by remote control to guide the embolus-delivery catheter extending therethrough to the mouth of the selected blood vessel or organ containing the target site.

Advantageously, the apparatus of the present invention permits a surgeon to embolize one or more vessels or organs in a body without using a guide wire to push an embolus into or through an embolus-delivery catheter to reach the target site in the body. A catheter used to deliver emboli is sometimes called an "introducer" catheter. Further, use of a stream of pressurized fluid to move am embolus from a hollow cartridge through an introducer catheter provides an embolus delivery system that is easily manageable by the surgeon during embolization. Such a hydraulic system offers many advantages in use because it operates to cause a uniform, predetermined force to be applied to an embolus on command during each embolization. This technique enhances a surgeon's ability to position an embolus properly at a target site in a vessel once the embolus has emerged from the distal end of a catheter.

Illustratively, the method and apparatus of the present invention can be used by a surgeon to perform a vein bypass of femoro-popliteal, femoro-tibial, or femoro-pedal arteries. After embolizing each side branch of a vein extending through the leg of a patient, the vein can be surgically reconfigured to function as an artery and "replumbed" to replace a malfunctioning artery that is unable to conduct an adequate flow of blood therethrough. Using the catheter-based embolus delivery system, vein side branch embolization is achievable without making a long incision along the length of the leg in accordance with present accepted medical practice.

Additional features and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 1 is a diagrammatic view of an embolus supply system in accordance with the present invention showing a feeder assembly having a hollow housing configured to hold many emboli, a delivery catheter coupled to an embolus-discharge outlet on the housing, and a pressurized fluid system coupled to an inlet on the housing to permit a stream of pressurized fluid to enter the housing and carry a selected embolus contained therein into the delivery catheter;

FIG. 1a is a diagrammatic view of an actuator means in the pressurized fluid system illustrated in FIG. 1 showing the fluid switch after it has been moved to an "actuated" position to cause a stream of pressurized fluid to be routed from the pressure system to the inlet of the feeder assembly;

FIG. 2 is a top plan view of the housing of FIG. 1 with portions broken away to reveal a magazine that is movable on guide rails provided inside the housing to position each of the many embolus cartridges one at a time in an "embolus-discharging" position located between the housing inlet and outlet;

FIG. 3 is a side elevation view of the housing with portions broken away to show a section (along line 3—3 of FIG. 2) of the interior of the housing containing the movable magazine;

FIG. 4 is a top plan view of one of the many embolus cartridges loaded into the movable magazine with portions broken away to show a "straightened" coiled spring embolus stored in a through passageway formed in the embolus cartridge in a position ready to be discharged therefrom;

FIG. 5 is an enlarged view of a portion of the housing of FIG. 2 showing use of pressurized fluid in the housing inlet to move a piston and a drive bar coupled to the piston to a projected position so that the magazine is advanced one-half step in its direction of travel and moved to disengage the guide rails and one of the embolus cartridges in the magazine is moved with the magazine to engage the housing outlet;

FIG. 6 is a view of a portion of the housing of FIG. 5 coupled to a delivery catheter and enlarged to show discharge of a spring embolus from an embolus cartridge into a delivery catheter upon admission of a stream of pressurized fluid into the through passageway of an embolus cartridge situated in an embolus-discharging position;

DETAILED DESCRIPTION OF THE DRAWINGS

During vascular surgery, surgeons often find it necessary to occlude or ligate certain veins, arteries, or collateral blood vessels to control blood flow through the body undergoing an operation. Typically, the blood vessels collateral to the saphenous vein in the leg must be ligated during vascular surgery to reconfigure the vein to function as an artery. Of course, it is also desirable to occlude body organs other than blood vessels in the course of other surgical procedures.

The improved apparatus of the present invention advantageously is well-suited for delivering coil emboli to a vessel in a simple, efficient, repeatable, and predictable manner. Means is provided for inserting an embolus into an introducer catheter quickly and easily and also discharging the embolus from the introducer catheter into a selected vessel in a body using either pressurized fluid or a guide wire.

A system 10 for transcatheter embolization of selected vessels or organs in a body is illustrated in FIG. 1. Advantageously, this system 10 is well-suited for delivering a coil embolus 12 (or other embolus) to a target site in a body vessel or organ. Once it reaches the target site, the coil embolus 12 partly occludes the vessel and causes a blood clot to "organize" around the coil embolus 12 at the target site. Later, the blood clot becomes solid with ingrowth of cells and fibrous tissue to occlude the vessel totally. It will be appreciated that the system 10 could be used to deliver various emboli other than coil emboli 12.

Figure 14:
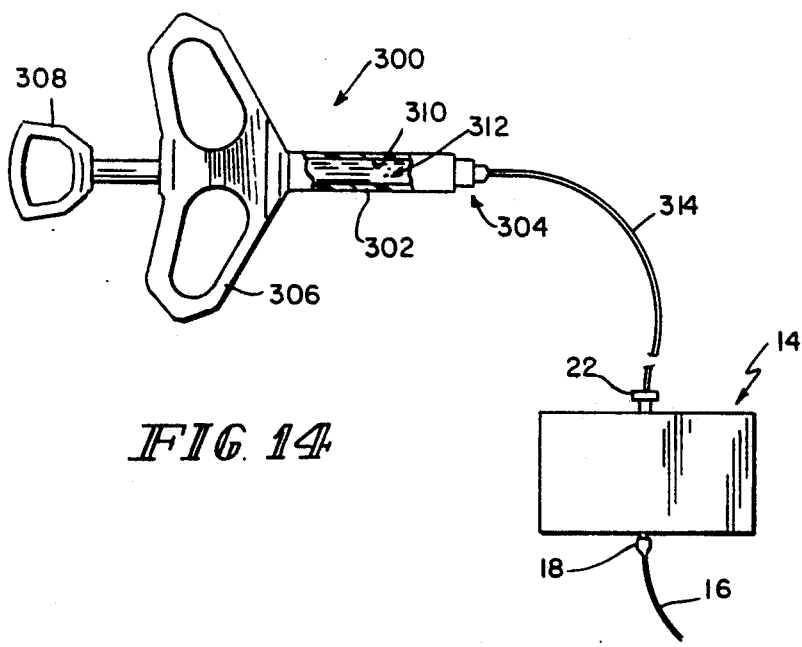
FIG. 14 is a diagrammatic illustration of yet another embodiment of the present invention wherein syringe means is used to deliver a stream of pressurized fluid into an embolus feeder assembly.

Embolus-delivery system 10 includes a feeder assembly 14, an introducer catheter 16 coupled to an outlet fixture 18 of the feeder assembly 14, and a fluid supply assembly 20 coupled to an inlet fixture 22 of the feeder assembly 14. The fluid supply assembly 20 is used to deliver a stream of pressurized fluid into the interior region 24 of feeder assembly 14 to move an embolus 12 out of its home therein and into and trough introducer catheter 16 toward its destination outside of the introducer catheter 16 in a blood vessel or the like. System 10 renders obsolete any need to use a guide wire or other instrument to load an embolus into an introducer catheter and discharge an embolus from an introducer catheter. In the alternative embodiment of FIG. 14, syringe means 300 is used to generate a stream of pressurized fluid and a tube 314 is used to deliver that stream of pressurized fluid into the interior region of feeder assembly 14 to discharge an embolus therein into introducer catheter 16.

Fluid supply assembly 20 includes a fluid reservoir 26, a pressure system 28, a waste fluid reservoir 29, and an actuator means 30. The actuator means 30 is operable manually or by remote control to cause either a stream of pressurized fluid from fluid reservoir 26 to be injected into the feeder assembly 14 or a volume of waste fluid from the feeder assembly 14 to be routed to the waste fluid reservoir 29. Pressure system 28 pressurizes fluid in fluid reservoir 26 to generate a source of pressurized fluid that can be injected into the feeder assembly 14 at the command of the surgeon. The surgeon need only activate the actuator means 30 of fluid supply assembly 20 to cause a stream of pressurized fluid to be injected through inlet fixture 22 into feeder assembly 14.

Actuator means 30 is operable to control whether fluid flows into or out of feeder assembly 14. The actuator means 30 illustratively includes a two-position fluid switch 31 having a first stage fluid-channeling means 32 and a second stage fluid-channeling means 34. Each of these fluid-channeling means 32, 34 is shown diagrammatically in FIGS. 1 and 1a. Fluid switch 31 is movable between a "normal" waste fluid-discharge position shown in FIG. 1 and a pressurized fluid-input position shown in FIG. 1a.

In its "normal" position, the first stage fluid-channeling means 32 of fluid switch 31 operates as shown in FIG. 1 to conduct waste fluid discharged from the feeder assembly 14 to the waste fluid reservoir 29. The waste fluid is conducted from feeder assembly 14 through a transfer conduit 36 coupled to an inlet tube 38 of inlet fixture 22, fluid switch 31, and a waste conduit 40 coupled to waste fluid reservoir 29. Of course, waste conduit 40 could instead be coupled to fluid reservoir 26 if it is advantageous to recycle the fluid used to operate system 10.

Essentially, the first stage fluid-channeling means 32 in fluid switch 31 includes a passageway 41 configured to interconnect transfer conduit 36 and waste conduit 40 so that waste fluid can flow therebetween. The first stage means 32 also includes a closure mechanism 43 configured to close a supply conduit 42 coupled to fluid reservoir 26 to block discharge of pressurized fluid therefrom. Accordingly, in the normal position of fluid switch 31 shown in FIG. 1, the supply conduit 42 that is coupled to the fluid reservoir 26 is not ale to supply pressurized fluid to the feeder assembly 14. Therefore, no pressurized fluid is introduced into the feeder assembly 14. A return spring 44 or the like is provided and arranged to yieldably bias the fluid switch 31 to assume the normal position shown in FIG. 1.

The actuator means 30 also includes push-button means 44 or the like for moving the two-position fluid switch 31 against the biasing force provided by return spring 44 to assume the pressurized fluid input position as shown illustratively in FIG. 1a. In this position, the second stage fluid-channeling means 34 in fluid switch 31 operates to conduct a stream of pressurized fluid discharged from fluid reservoir 26 to the feeder assembly 14 via the supply conduit 42 and the transfer conduit 36. This stream of pressurized fluid is routed along a predetermined path (described in more detail below) through the interior region 24 of the feeder assembly 14 so that it intercepts a single embolus 12 contained therein and flushes that embolus 12 out of the feeder assembly 14 through the outlet fixture 18 and into the introducer catheter 16. The use of a stream of pressurized fluid to flush an embolus 12 out of feeder assembly 14 and into an introducer catheter 16 is shown best in FIG. 6.

Essentially, the second stage fluid-channeling means 34 in fluid switch 31 includes a passageway 48 configured to interconnect transfer conduit 36 and supply conduit 42 so that pressurized fluid can flow therebetween. The second stage means 34 also includes a closure mechanism 50 configured to the close waste conduit 40. Once the push-button means 44 is manually or automatically released, the return spring 44 operates to move the fluid switch 31 from its pressurized fluid-input position shown in FIG. 1a to its normal waste fluid-discharge position shown in FIG. 1.

Feeder assembly 14 is illustrated in more detail in FIGS. 2 and 3. A movable magazine 52 is situated in the interior region 24 of feeder housing 54 and configured to hold several embolus cartridges 56 side by side one another. As shown best in FIG. 4, each embolus cartridge 56 is formed to include a passageway 58 extending therethrough and containing a coil embolus 12 that has been "straightened" somewhat to fit and remain in passageway 58 until a stream of pressurized fluid is injected into passageway 58 to dislodge and discharge the embolus 12. Each embolus cartridge 56 also includes an enlarged outlet head 60 at its front end and an enlarged inlet head 62 at its rear end. When each cartridge 56 is loaded into a mounted position in magazine 52 as shown in FIG. 2, the inlet head 62 abuts a first cartridge support wall 64 on magazine 52, the outlet head 60 abuts a second cartridge support wall 66 on magazine 52, and the elongated shaft 68 extending between inlet and outlet heads 62, 60 extends across the width of magazine 52.

As shown in FIG. 4, an embolus 12 is deposited in the cartridge passageway 58 in, for example, a central region 57 so that it is ready to be discharged through outlet head 60 whenever it is "hit" by the slug of fluid expelled from fluid supply assembly 20. As shown in FIG. 4, embolus 12 is initially packed into passageway 58 to load the cartridge 56. In the case of a coiled spring embolus 12, it is unraveled to assume a somewhat straight shape and loaded into the passageway 58 during factory assembly of cartridge 56. Essentially, the coiled spring 12 is uncoiled or straightened to assume a packed position in the passageway 58 and configured to exert a light predetermined force against the interior wall of the passageway 58 to retain the spring 12 in the cartridge 56 until a stream of pressurized fluid 32 is injected into passageway 58.

It will be appreciated that a variety of coiled spring emboli are available in the marketplace. Presently, a helical coil or curled segment made of small diameter platinum wire without any fiber tails or threads attached thereto is the preferred embolus to use in connection with embolus-delivery system 10. For example, suitable coil emboli are available from Target Therapeutics, Inc. of San Jose, Calif.

As shown in FIG. 4, a coiled spring embolus 12 can be uncoiled and straightened using suitable automated or manual means to permit loading into the cartridge passageway 58. Such an embolus 12 is retained temporarily in a fixed position in passageway 58 by frictional engagement of the coiled spring embolus 12 against the interior wall. The internal diameter of passageway 58 is matched to the size of embolus 12 to be retained therein to ensure that the straightened spring embolus 12 is unable to move to assume its original helical or coiled shape. However, injection of a stream of pressurized fluid into the inlet head 62 of passageway 58 at a sufficient rate will apply enough work to the spring 12 to overcome frictional forces between the spring 12 and the passageway wall, thereby dislodging the spring 12 and discharging it from cartridge 56 through outlet head 60. Once spring 12 emerges from the introducer catheter 16 at the target site in a vessel, it will coil or "reform" to assume a coiled shape similar to its original helical shape as shown in FIGS. 1 and 6.

The magazine 52 is configured to hold a series of embolus cartridges 56 in side-by-side spaced-apart parallel relation as shown in FIG. 2. The magazine 52 is movable inside feeder housing 54 along guide rails 70, 72 in forward direction 74 to place each embolus cartridge 56 one at a time in an embolus-discharging position or station (shown in FIG. 5) between inlet fixture 22 and outlet fixture 18. In the embodiment shown in FIGS. 1–8, means is provided in the inlet fixture 22 for using a stream of pressurized fluid supplied by the pressure system 28 and introduced into inlet tube 38 to move the magazine 52 in the forward direction 74 on guide rails 70, 72 and in the sideways direction 76 away from guide rails 70, 72 so that each embolus cartridge 56 in the magazine 52 is aligned in sequence one at a time in the embolus-discharging position within the feeder housing 54.

As will be explained in more detail below, once the magazine 52 is moved to align an embolus cartridge 56 in the embolus-discharging position shown in FIG. 5, some of the pressurized fluid received in inlet fixture 22 is injected into the through passageway 68 formed in cartridge 56 to dislodge the coil embolus 12 provided therein and flush the embolus 12 out of cartridge 56 and into and through the introducer catheter 16 coupled to outlet fixture 18. This same pressurized fluid has sufficient velocity to transport the embolus 12 through the introducer catheter 16 and expel the embolus 12 from catheter 16 to reach a target destination in a blood vessel (not shown) or the like.

Inlet fixture 22 includes a cylinder 78 formed to include a cylindrical closed chamber 80 sized to receive a reciprocable sealed piston 82 therein as shown, for example, in FIGS. 2, 5, 6, and 7. A first spring 84 is provided in closed chamber 80 for yieldably biasing piston 82 toward the inlet tube 38 against a seat 86 positioned near the inlet end of cylinder 78. Injection of a stream of pressurized fluid through inlet tube 38 into closed chamber 80 of cylinder 78 will cause the piston 82 to move against the biasing force of first spring 84 to a projected position shown in FIG. 5 so that the space 88 in closed chamber 80 between inlet tube 38 and piston 82 will fill with pressurized fluid 90 received from fluid reservoir 26.

As shown best in FIGS. 5 and 6, piston 82 and a tubular shaft 92 appended thereto are formed to include a passageway extending therethrough for conducting pressurized fluid 90 from space 88 in cylinder 78 into the through passageway 58 formed in the embolus cartridge 56. An axially outer small diameter aperture 94 and an axially inner larger diameter aperture 96 formed in piston 82 and a longitudinally extending aperture 98 formed in tubular shaft 92 cooperate to define the passageway through piston 82 for conducting pressurized fluid 90 from cylinder 78 to embolus cartridge 56.

A valve assembly is provided in piston assembly 82, 92 for controlling passage of pressurized fluid through the piston passageway 94, 96, 98. Valve assembly includes a ball valve 110 in the large diameter aperture 96 in the piston 82 and a spring 112 in the longitudinally extending aperture 98 in tubular shaft 92. As shown in FIG. 5, spring 112 acts against a ledge inside the tubular shaft 92 to yieldably bias ball valve 110 into engagement with a valve seat in the large diameter aperture 96 to block the flow of pressurized fluid 90 from the small diameter aperture 94 into the large diameter aperture 96 and longitudinally extending aperture 98.

It will be appreciated that the spring 112 is strong enough so that it will not yield and allow pressurized fluid 90 to move from the space 88 in cylinder 78 past the ball valve 110 and into the through passageway 58 in embolus cartridge 56 until after the outlet head 60 of embolus cartridge 50 is moved to establish a leak-free sealed connection with the outlet fixture 18. Otherwise, pressurized fluid 90 injected from cylinder 78 into the through passageway 58 in embolus cartridge 56 might inadvertently leak into the interior region 24 of the feeder housing 54 instead of passing directly into the outlet fixture 18 on its way into the lumen of the introducer catheter 16. As shown best in FIG. 6, the distal end of tubular shaft 92 is sized and shaped to mate in sealing engagement with the open end of the inlet head 62 on the embolus cartridge 56 so that pressurized fluid 90 admitted into longitudinally extending aperture 98 is able to flow directly into the through passageway 58 formed in embolus cartridge 56 without leaking.

Outlet fixture 18 includes a catheter mounting socket 114 and an embolus discharge tube 116. The catheter mounting socket 114 extends through a side wall of the feeder housing 54 and includes an outwardly facing nipple 118 sized to connect to an introducer catheter 16 as shown in FIG. 2. Embolus discharge tube 116 is appended to an inwardly facing part of catheter mounting socket 114. Discharge tube 116 and mounting socket 114 cooperate to provide a passageway 120 shown best in FIG. 6 for conducting an embolus 12 and the pressurized fluid 90 expelled therewith from the through passageway 58 of the embolus cartridge 56 into the downstream introducer catheter 16. It will be appreciated that the first cartridge support wall 64 has an inner side 119 that sealingly mates with the downstream end of each cartridge head 60, an outer side 121 having an outlet nipple 122 for each cartridge 56 that is able to sealingly mate with the upstream end of embolus discharge tube 116, and a short conduit 124 for conducting the embolus 12 (and pressurized fluid 90 expelled therewith) discharged from cartridge 56 in a downstream direction into embolus discharge tube 116.

A magazine return mechanism 126 is mounted on an inside wall of feeder housing 54 adjacent to outlet fixture 18 as shown in FIGS. 2, 5, 6, and 8. Magazine return mechanism 126 includes a guide clip 128 having a leading edge 130 positioned to lie in spaced-apart parallel relation to one of the guide rails 70 inside feeder housing 54 as shown best in FIGS. 3, 5, and 6. A pair of springs 132 act between an upstanding wall 134 on guide clip 128 and catheter mounting socket 114 to yieldably bias guide clip 128 to its projected position shown in FIG. 2.

A guide bar 136 is appended to the bottom wall of magazine 52 as shown in solid lines in FIG. 3 and in phantom lines in FIGS. 2, 5, 6, and 8. Guide bar 136 is sized to fit and slide in the space between the leading edge 130 of guide clip 128 and the side edge 138 of guide rail 70. Although springs 132 do yieldably urge the leading edge 130 of guide clip 128 into engagement with guide bar 136 on magazine 52, such engagement will not substantially obstruct or otherwise hinder sliding movement of magazine 52 along guide rails 70, 72 in the forward direction 74 as it moves to remove an "empty" embolus cartridge 56 from the embolus-discharging position and replace it with an adjacent "loaded" embolus cartridge. Springs 132 will be compressed during movement of magazine 52 in the sideways direction 76 as the guide bar 136 is pushed against the leading edge 130 of guide clip 128 during movement of magazine 52 under a load from its normal position shown in FIGS. 2 and 8 to its embolus-discharging position shown in FIGS. 5 and 6. The springs 132 and guide clip 128 cooperate to return magazine 52 to its normal position engaging guide rails 70, 72 once the movement-inducing load is removed from magazine 52. In the illustrated embodiment, tubular shaft 92 is periodically moved in sideways direction 76 to apply such a movement-inducing load to magazine 52.

A drive bar 140 is appended to the piston 82 to move therewith and is reciprocable in sideways direction 76 and 77 to cause magazine 52 to move in forward direction 74. As shown in FIGS. 2 and 3, drive bar 140 extends through a slot formed in magazine 52 to pass underneath the guide rail 70 closest to inlet fixture 22. Drive bar 140 includes a pawl 142 at its distal end. Pawl 142 is oriented to project into a serpentine slot 144 formed in magazine 52 and move therein to control movement of magazine 52 in forward direction 74.

Figure 7:
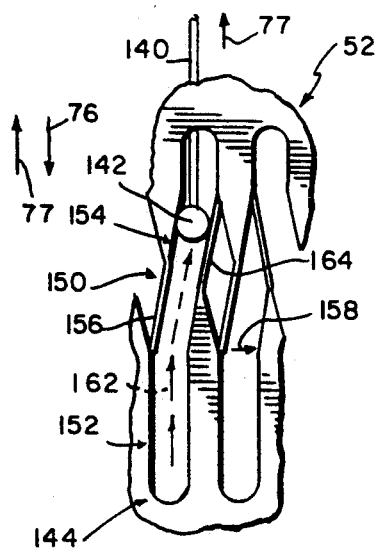
FIG. 7 is a view of a portion of the movable magazine shown in FIG. 5 enlarged to show the direction of travel of a drive bar as it moves with the piston to a retracted position following discharge of an embolus so that the magazine is advanced one-half step in its direction of travel and moved to reengage the guide rails provided in the housing.
Figure 7A:
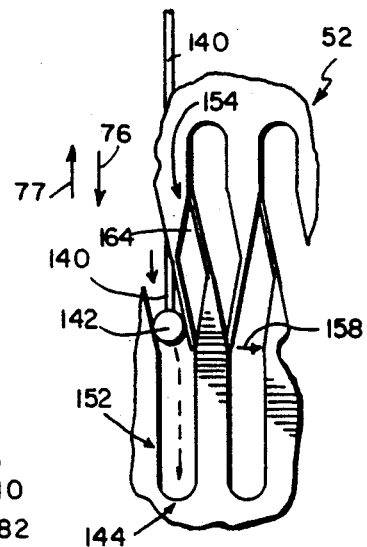
FIG. 7a is a view similar to FIG. 7 showing the direction of travel of the drive bar as it moves with the piston to a projected position so that the magazine is advanced one-half step in its direction of travel and moved to disengage the guide rails provided in the housing.
Figure 8:
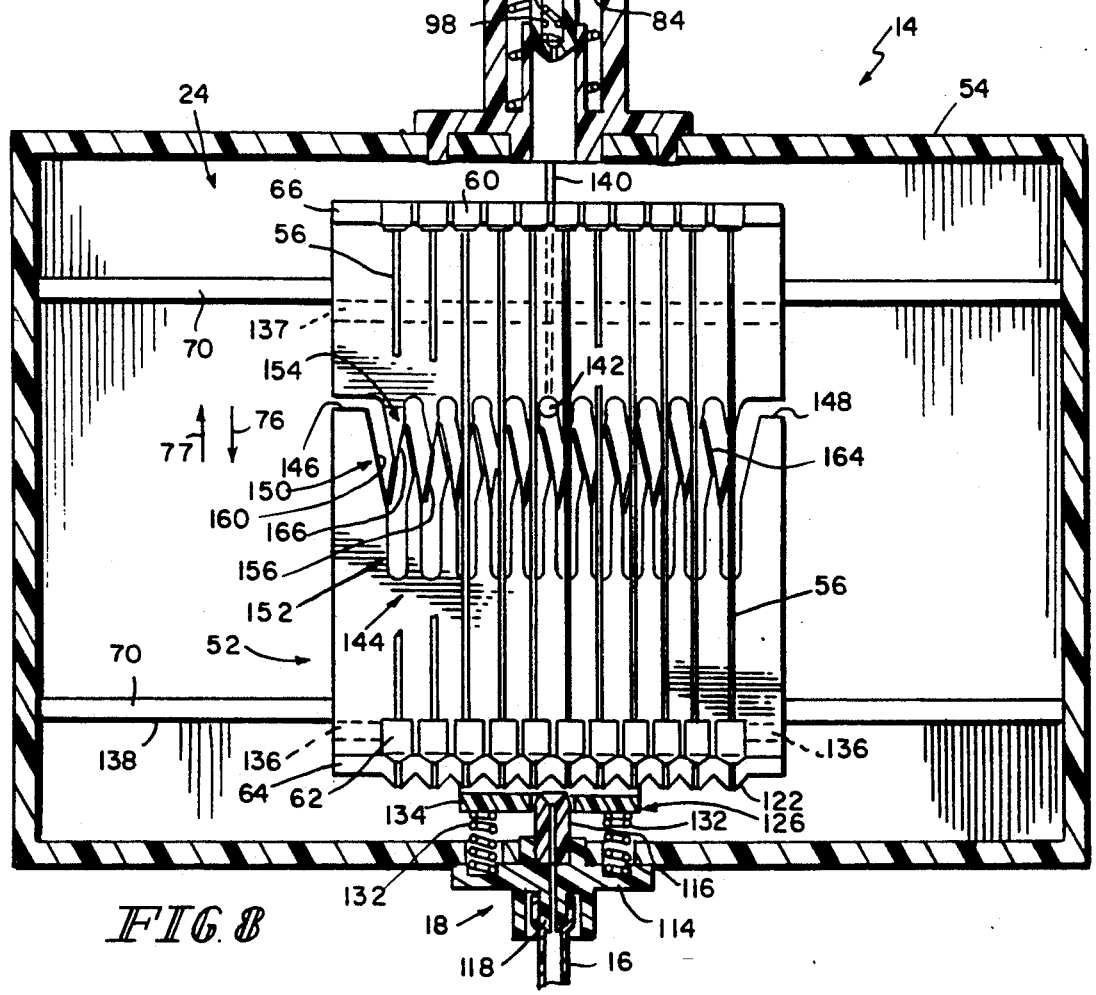
FIG. 8 is a view similar to FIG. 5 showing the location of the magazine in the housing after the system has been operated to discharge an embolus from each of the first five embolus cartridges carried in the magazine and prior to movement of the magazine relative to the guide rails to place the sixth embolus cartridge in the embolus-discharging position so that the embolus contained therein can be discharged into the delivery catheter coupled to the housing outlet.

As shown best in FIGS. 2, 5, and 8, the serpentine slot 144 includes an inlet 146 at one end and an outlet 148 at the other end. A series of Y-shaped passages are joined together as if "holding hands" to form the serpentine shape of slot 144. Each Y-shaped passage includes an entry arm 150, a base leg 152, an exit arm 154, and a one-way gate 156 mounted in the passage between entry arm 150 and base leg 152 for pivotable movement therein. The proximal edge of one-way gate 156 is pivotably appended to a portion of magazine 52 situated between entry arm 150 and exit arm 154 so that one-way gate 156 can swing in direction 158 from its normally closed position shown in FIGS. 2, 5, 7, and 8, to an opened position shown in FIG. 7a..

One-way gate 156 opens to let pawl 142 pass from entry arm 150 into base leg 152 during movement of piston 82 and drive bar 140 in sideways direction 76 as cylinder 78 fills with pressurized fluid. However, one-way gate 156 closes as shown in FIG. 7 to cause pawl 142 to move from base leg 152 into exit arm 154 in response to movement of piston 82 and drive bar 140 in sideways direction 77 as cylinder 78 is emptied of waste fluid. Such closure of one-way gate 156 blocks pawl 142 from being returned to entry arm 150 in response to movement of piston 82 and drive bar 140 in sideways direction 77.

OPERATION

A cycle of operation of embolus-delivery system 10 is illustrated in sequence in FIGS. 2, 5, and 6. The location of magazine 52 inside feeder housing 54 at the beginning of a cycle is shown in FIG. 2. Cylinder 78 does not yet contain any pressurized fluid and a single embolus 12 is lodged temporarily in embolus cartridge 56. Fluid switch 31 is maintained by return spring 42 in its waste fluid-discharge position as shown in FIG. 1 to block admission of any pressurized fluid 90 from fluid supply assembly 20 into embolus cartridge 56.

An embolus 12 can be discharged hydraulically from embolus cartridge 56 into delivery catheter 16 in the following manner. Push-button means 46 is pressed, for example, to move fluid switch 31 to its pressurized fluid-input position shown in FIG. 1a. A stream of pressurized fluid is now free to flow from fluid reservoir 26 into the space 88 in cylinder 78 above the piston 82 This surge of pressurized fluid will move piston 82 against spring 84 in sideways direction 76 and move the drive bar 140 appended to piston 82 in the same direction. During such movement the pawl 142 at the end of drive bar 140 will engage the camming surface 160 which forms a side wall of entry leg 150. As pawl 142 moves in a straight line in direction 76, it will impart a force to cause magazine 52 to slide on guide rails 70, 72 in forward direction 74. Magazine 52 is moved by pawl 142 an increment of one-half step in forward direction 74 so that the outlet head 60 of the embolus cartridge 56 that is being moved into the embolus-discharging position is moved to lie in opposing relation to the inlet opening of the embolus discharge tube 116 coupled to outlet fixture 18.

While magazine 52 is moving in forward direction 74 along guide rails 70, 72 due to camming action of pawl 142 against camming surface 160, the tubular shaft 92 moves in sideways direction 76 with the piston 82 to engage the inlet head 62 of the embolus cartridge 56 to be loaded into the embolus-discharging position. Tubular shaft 92 pushes the magazine 52 toward outlet fixture 18 to cause the outlet head 60 of said cartridge 56 to be coupled to the inlet end of embolus discharge tube 116 so that an embolus 12 contained in the cartridge 56 can be discharged into delivery catheter 16 through embolus discharge tube 116. As shown best in FIG. 5, the guide bars 136, 137 of magazine 52 disengage guide rails 70 and guide bar 136 is pushed against the leading edge 130 of guide clip 128 to compress clip-biasing springs 132.

As long as cylinder 78 is filled with pressurized fluid 90 and piston 82 remains in its projected position shown in FIGS. 5 and 6, the outlet nipple 122 of the first cartridge support wall 64 of magazine 52 will remain in sealing engagement with the embolus discharge tube 116 to establish a discharge passageway 58, 124, 120 into the lumen of delivery catheter 16. Embolus 12 will remain in embolus cartridge 56 until the magnitude of the fluid pressure in cylinder 78 rises to a level sufficient to move ball valve 110 against spring 112 to its opened position shown in FIG. 6 Once that valve 110 is opened, a stream of pressurized fluid 90 will flow from space 88 in cylinder 78 through the longitudinally extending aperture 98 formed in tubular shaft 92 into the through passageway 58 in embolus cartridge 56. This fluid stream will act to dislodge the single embolus 12 contained in passageway 58 and carry it out of cartridge 56 and into delivery catheter 16 on route to a target site in a blood vessel or the like at the distal end of catheter 16.

Once the embolus 12 has been discharged hydraulically from the first embolus cartridge 56 and push-button means 46 is released, return spring 42 on actuator means 30 will return fluid switch 31 to its normal waste fluid-discharge position shown in FIG. 2. As shown in FIG. 1, the fluid chamber 88 in cylinder 78 is now coupled to waste fluid reservoir 29 via transfer conduit 36, passageway 41, and waste conduit 40. The guide clip 128 and springs 132 of magazine return mechanism 126 cooperate to push magazine 52 back in sideways direction 77 to reestablish engagement of guide bars 136, 137 and guide rails 70. As shown best in FIG. 7, such movement of magazine 52 causes pawl 142 to move along path 162 in serpentine slot 144 from base leg 152 through the exit arm 154 into the entry arm 150 of an adjacent Y-shaped passage. One-way gate 156 blocks return movement of pawl 142 into the first entry arm 150.

Drive rod 140 is pushed in sideways direction 77 as pawl 142 is forced to move along path 162 to cause tubular shaft 92 to disengage the inlet head 60 of the first embolus cartridge 56 and piston 82 to force most of the pressurized fluid 90 out of the space 88 in cylinder 78. As noted above, this discarded fluid is conducted through waste conduit 40 and deposited in waste fluid reservoir 29. As shown in FIG. 7, pawl 142 moves past a second one-way gate 164 pivotably appended to magazine 52 on its way to a new "home" position in the adjacent entry arm 150. (For example, pawl 142 is shown in one of its home positions in FIG. 8.) It will be appreciated that this second one-way gate 164 blocks reentry of pawl 142 directly into exit arm 154 during a next cycle of operation. Also, it will be understood that movement of pawl 142 along path 162 will cause magazine 52 to move another increment of one-half step in forward direction 74 due to camming engagement of pawl 142 and camming surface 166 in exit arm 154. Now pawl 142 has moved magazine 52 one full step along guide rails 70, 72 to complete one cycle of operation.

A purge valve assembly 168 is provided on cylinder 78 to purge air from inside cylinder 78 prior to the first operation cycle of system 10. Purge valve assembly 168 includes a discharge conduit 170, a valve 172, and a biasing spring 174 in the discharge conduit 170.

Figure 9:
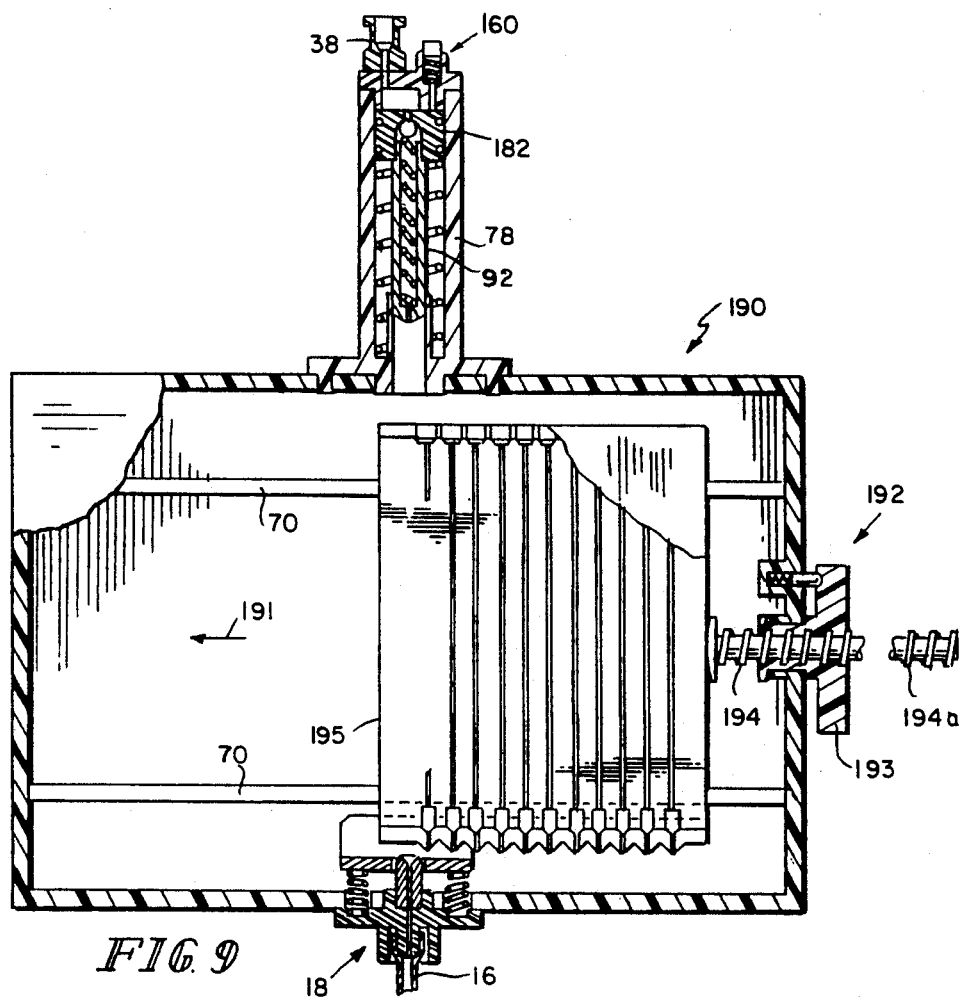
FIG. 9 is a top plan view of another embodiment of a housing containing a magazine that is movable along guide rails provided in the housing by means of a mechanical screw instead of a hydraulically actuated linkage of the type disclosed in the embodiment of FIGS. 1-8.

In another embodiment illustrated in FIG. 9, an alternative embolus discharge system 190 is shown to include a mechanical magazine advancing assembly 192 instead of the hydraulically actuated system shown in FIGS. 1-8. Assembly 192 includes, for example, a rotatable handle 193 rotatably mounted in a side wall of the feeder housing and a screw 194 fixed to rotate with handle 193 and push against movable magazine 195. Handle 193 can be rotated to rotate screw 194 and advance magazine 195 in direction 191 in one step increments in the feeder housing. A spring-loaded detent assembly 196 can be provided as shown in FIG. 9 to engage a series of circumferentially spaced-apart notches in the underside of handle 193 to control the actual length of each incremental movement of magazine 195 in direction 191. Also, an extension 194a of screw 194 can be coupled to other manual or automatic rotating means (not shown) to control advance of magazine 195 in direction 191. It is within the scope of the present invention to use any suitable mechanical linkage configured to move magazine 195 incrementally in direction 191 to align the cartridges 56 in magazine 195 in an embolus-discharging position within feeder box 190.

Figure 13:
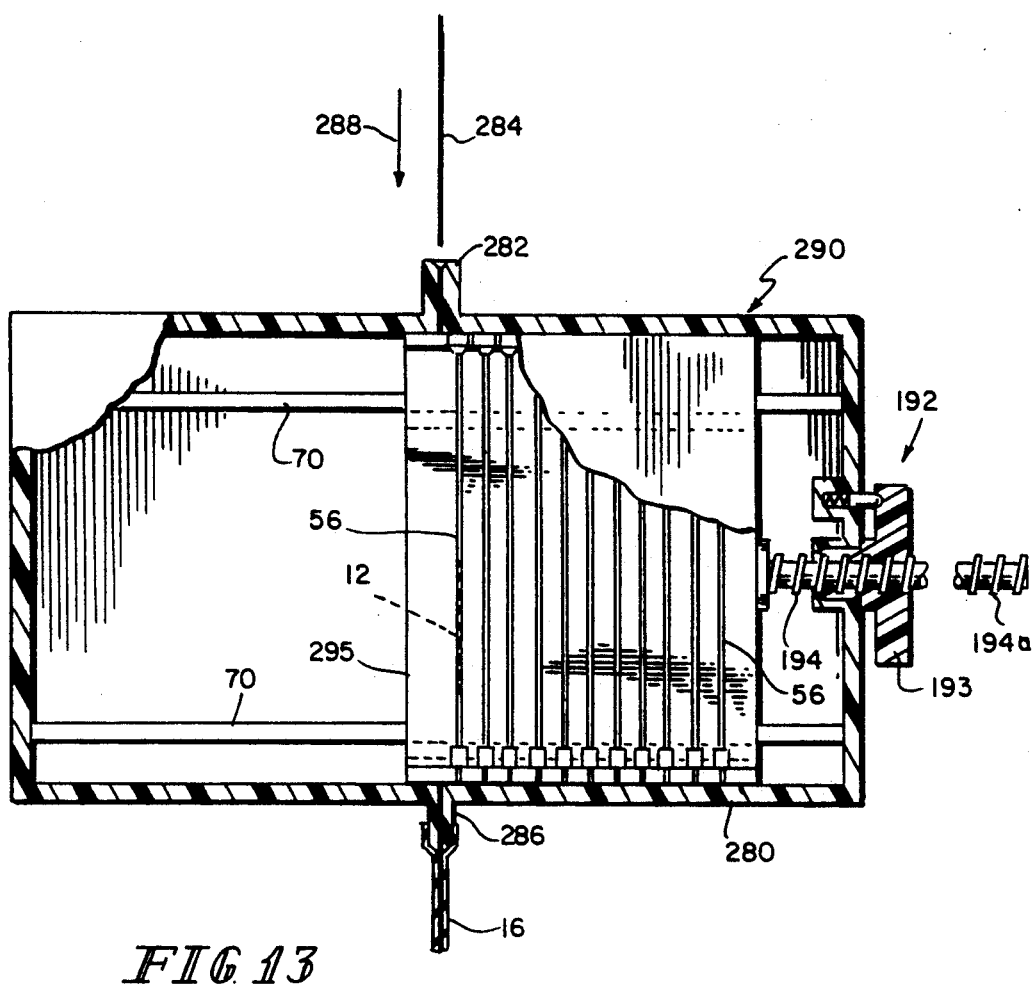
FIG. 13 is a view of another embodiment of the present invention showing a magazine containing a plurality of emboli, a mechanical linkage for moving the magazine inside its housing, and a guide wire that is movable into the magazine to discharge one of the emboli from the magazine.

In still another embodiment illustrated in FIG. 13, an alternative embolus discharge system 290 is shown to include an assembly 192 (like the assembly shown in FIG. 9) for mechanically advancing magazine 295 along rails 70 inside feeder housing 280. Feeder housing 280 includes an inlet 282 for receiving a guide wire 284 and an outlet 286 for receiving the guide wire 284 and an embolus 12 discharged from magazine 295. As in previous embodiments, magazine 295 includes a plurality of cartridges 56 and each cartridge 56 is formed to include a hollow passageway containing a single embolus 12. Of course, magazine 295 could alternatively be moved inside feeder housing 280 manually or using other mechanical or electrical means.

A conventional guide wire 284 is movable in direction 288 to enter inlet 282 and the passageway of a cartridge 56 aligned with inlet 282. The embolus 12 can be expelled from cartridge 56 into catheter 16 in response to movement of guide wire 284 in direction 288 to engage embolus 12 and push it out of magazine 295 through outlet 286. It will be understood that the guide wire 284 could then be moved further in direction 288 to move expelled embolus 12 all the way through catheter 16 such that the embolus 12 is expelled from catheter 16 and deposited at a destination outside of catheter 16.

In yet another embodiment illustrated in FIG. 4, syringe means 300 is provided to generate a stream of pressurized fluid that is delivered into feeder assembly 14 through hose 314. Syringe means 300 includes a hollow barrel 302 having a nozzle 304 at one end and a handle 306 at the other end. A plunger 308 is inserted into the handle end of the barrel 302 as is movable therein to pressurize a predetermined volume of fluid 312 contained in reservoir 310 therein and discharge that fluid 312 from the hollow barrel 302 through the nozzle 304. A hose assembly 314 interconnects nozzle 304 of syringe means 300 and the inlet fitting 22 of feeder assembly 14 to conduct a stream of pressurized fluid discharged from the nozzle 304 into one of the embolus-containing cartridges provided in feeder assembly 14. This stream of pressurized fluid dislodges an embolus and discharges it into catheter 16 in the manner described above.

Figure 10:
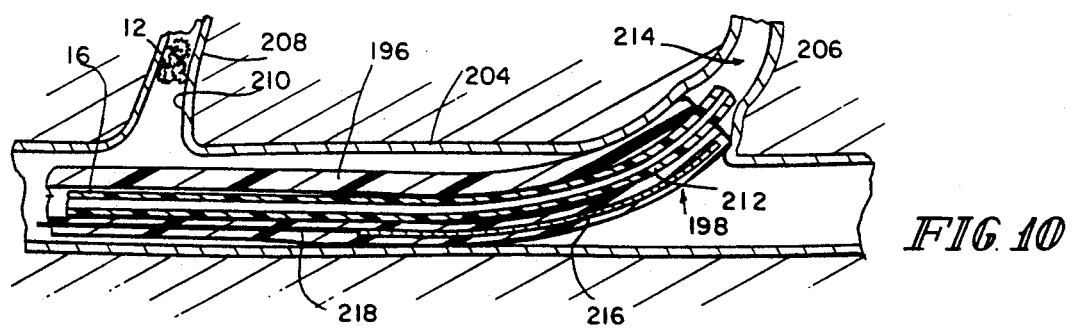
FIG. 10 is a sectional view of the distal end of the system of FIG. 1 in place in a main body vessel (e.g., vein or artery) showing how the introducer catheter is aimed into a collateral vessel selected to be occluded prior to delivery of an embolus through the introducer catheter to the target site in the selected collateral vessel and also showing another collateral vessel previously plugged by a reformed coil embolus.
Figure 11:
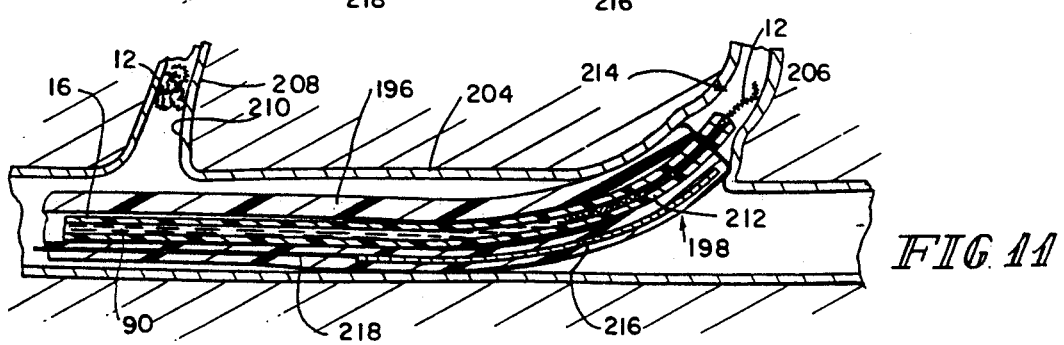
FIG. 11 is a view similar to FIG. 10 showing use of a stream of pressurized fluid to move a "straightened" coil embolus through the introducer catheter toward the target site in the selected collateral vessel.
Figure 12:
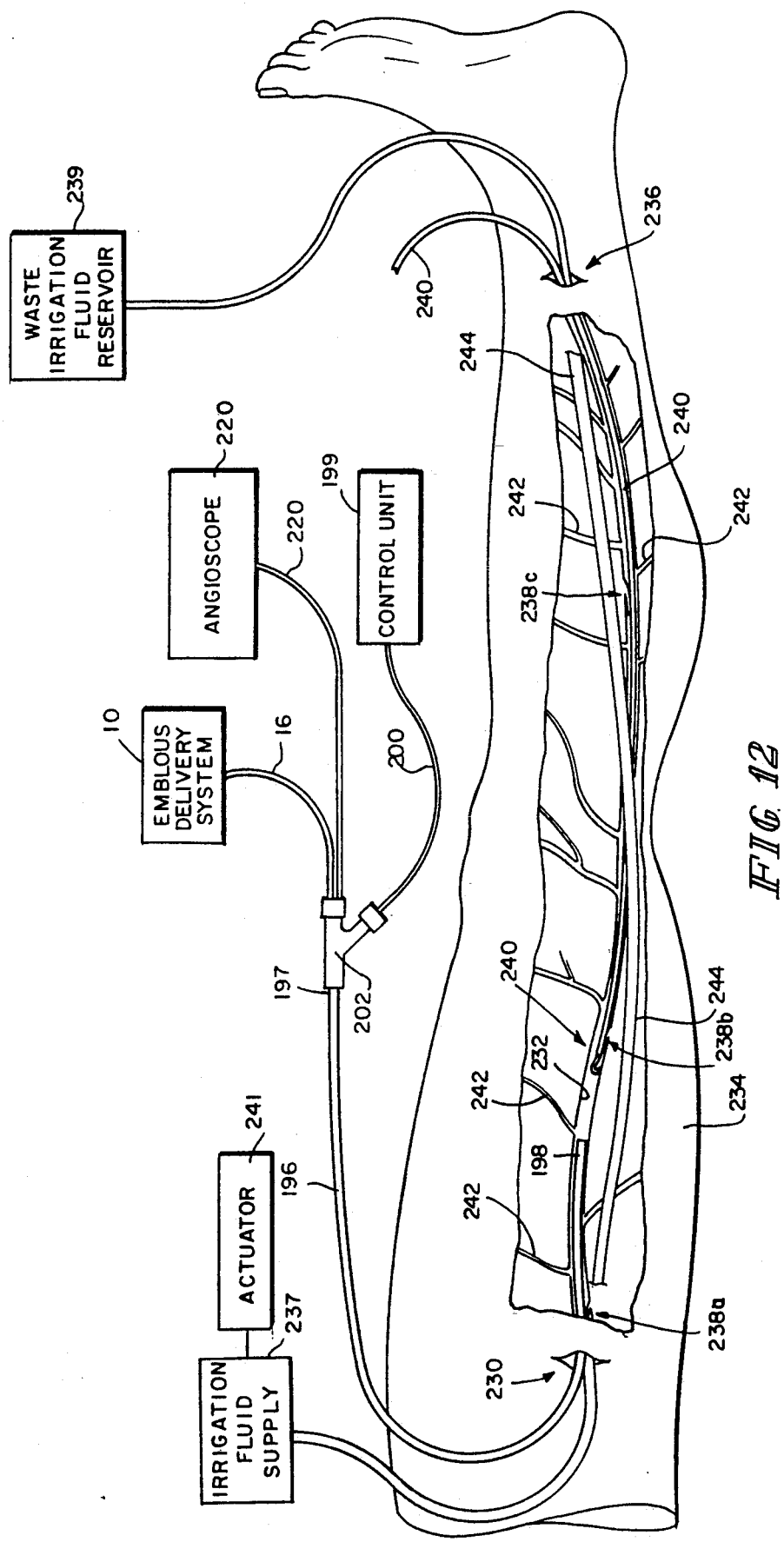
FIG. 12 is a diagrammatic illustration of a human leg in surgery to reconfigure a vein in the leg to function as an artery so that the reconfigured vein can be used to replace one or more disabled arteries in the leg.

A steerable and aimable guide catheter 196 of the type available from Catheter Research, Inc. of Indianapolis, Ind. can be used to position introducer catheter 16 in a selected position in a body as shown, for example, in FIGS. 10-12. Guide catheter 196 includes an inlet fitting 197 at its proximal end and an outlet opening 198 at its distal end as shown best in FIG. 12. A control unit 199 is connected by wire harness 200 to a socket 202 provided on guide catheter 196. Control unit 199 provides remote control means to permit a surgeon to steer guide catheter 196 through body passages and aim the outlet opening 198 at selected targets within the body undergoing surgery.

Reference is hereby made to U.S. Pat. Nos. 4,543,090; 4,601,705; and 4,758,222 for descriptions of the structure, function, and operation of suitable steerable and aimable catheters. It will be appreciated that a variety of sizes, shapes, and kinds of guide catheters and guide wires could be used to guide introducer catheter 16 to its destination in a body and that, in certain circumstances, introducer catheter 16 could be moved in a body to reach its target site without using any other catheter to guide it. It should also be understood that a steerable and aimable guide catheter could be used by itself to deliver an embolus to a destination in a body without using any separate introducer catheter.

Delivery of an embolus 12 to a target site in a blood vessel using embolus-delivery system 10 is illustrated in FIGS. 10 and 11. The distal end 198 of guide catheter 196 inserted through a venotomy into a body is advanced into a main blood vessel 204 having a pair of collateral blood vessels 206, 208 branching out from the main blood vessel 204. Collateral vessel 208 contains a coil embolus 12 that is wedged against the interior wall 210 of collateral vessel 208 to anchor the coiled embolus 12 in place so that blood begins to clot and form a vessel-occluding thrombus (not shown) around coil embolus 12.

The guide catheter 196 is maneuvered using control unit 199 to insert the distal tip 212 of the introducer catheter 16 into the open mouth of the unoccluded collateral vessel 206 so that the distal tip 212 is aimed toward a target site 214 therein. The steerable and aimable guide catheter 196 is inserted into the collateral vessel 206 as well. Illustratively, a temperature-activated memory element 216 made of a shape-memory alloy is connected to a lead wire 218 and heated using control unit 199 to move the distal end of guide catheter 196 to assume the upwardly curved shape shown in FIGS. 10 and 11.

The introducer catheter 16 extends through the lumen of guide catheter 196 and is movable axially therein until a clamp (not shown) is tightened to grip the outer surface of introducer catheter 16 and prevent relative movement of introducer catheter 16 inside the lumen of guide catheter 196. Once introducer catheter 16 has been maneuvered to enter the mouth of collateral vessel 206 as shown in FIG. 10, then the clamp can be loosened to permit the surgeon to push the introducer catheter 16 forward so that its distal tip 212 extends a short distance out of the lumen of guide catheter 196 and into the collateral vessel 206 and faces target site 214. At this point, the introducer catheter 16 is locked by tightening the clamp to prevent movement of introducer catheter 16 relative to guide catheter 196.

Desirably, the inner diameter of the lumen in guide catheter 196 is large enough to contain an angioscope 220 (shown in FIG. 12) in addition to the introducer catheter 16. The angioscope 220 can be used to permit the surgeon to view the interior regions of the main and collateral blood vessels as the guide catheter is steered to reach the collateral vessel 206 sought to be occluded.

Once a surgeon is satisfied that the introducer catheter 16 is in a collateral vessel and aimed properly at the target site in the collateral vessel, the surgeon is free to use the actuator means 30 to inject a slug of fluid into the cartridge 56 at a rate sufficient to dislodge the embolus 12 from its fixed position in the cartridge passageway 58 and propel the embolus 12 into and through the lumen of the introducer catheter 16. The coil embolus 12 remains in a somewhat uncoiled and straightened packed shape as it travels through the lumen of the introducer catheter 16 and reforms to its helical coiled shape as soon as it emerges from the distal tip of the introducer catheter 16. Using this technique, coil emboli can be delivered to a target site in a collateral vessel using a pressurized fluid such as biocompatible saline or the like without resort to use of a guide wire to move a coil embolus 12 either into or through an introducer catheter 16. Of course, as shown in embodiment of FIG. 13, a guide wire 284 or the like could be used instead of pressurized fluid to discharge an embolus 12 from cartridge passageway 58 either into or through introducer catheter 16.

One suitable application of the method and apparatus of the present invention is to perform a medical procedure known as a vein bypass of femoro-popliteal, femoro-tibial, or femoro-pedal arteries. This surgery can reconfigure a vein to function as an artery so as to replace one or more occluded, diseased, or otherwise malfunctioning arteries.

In severe lower limb (leg) ischemia requiring surgery, the superficial femoral and proximal popliteal arteries are generally occluded. As an alternative to limb amputation, it is known to suture the proximal end of the saphenous vein end-to-side on the distal common femoral artery and the distal end of the graft end-to-side on the distal popliteal artery. Typically, it is necessary to "fillet" the leg by making a long incision along the length of the leg to expose and prepare the vein undergoing reconfiguration and its collateral blood vessels (side branches). It is then typically necessary to ligate the numerous side branches of the vein. It will be understood that conventional surgical procedures of this type are complex and difficult and may result in a lot of substantial incisions made into the body of the patient. Also, the healing process of patients treated using the conventional procedures are often long and impaired because many of the patients are old, diabetic, obese, or a combination thereof.

Embolus delivery system 10, 190, or 290 can be used in surgery to complete a vein bypass of femoro-popliteal, femoro-tibial, or femoro-pedal arteries. Essentially, introducer catheter 16 can be guided into the lumen of a selected vein and its side branches through a small incision made in the leg by itself or using the guide catheter. The delivery system 10, 190, or 290 is operated to deliver an occlusion coil or other embolus 12 to a destination in the side branch. This procedure can be repeated for each side branch of the vein. Advantageously, this type of embolization procedure can be used to occlude all of the side branches of a vein without necessarily filleting the leg to expose the entire vein and surgically ligating each side branch of the vein. Visualization of the vein and its side branches can be accomplished by angioscopy. Also, ultrasound techniques can be used to monitor the progress of this new embolization technique.

A portion of the vein bypass procedure accomplished using the embolus delivery system 10, 190, or 290 is illustrated in FIG. 12. For example, such a procedure involves the steps described in the following paragraphs. It will be understood that the use of system 10, 190, or 290 is not limited to surgical procedures on legs; rather system 10, 190, or 290 has great utility in surgical procedures involving other body parts and also in other non-surgical or non-medical procedures where it is advantageous to occlude a vessel.

Referring to FIG. 12, a first small incision 230 is made to open vein 232 in an upper portion of leg 234 near the groin area and a second small incision 236 is made in a lower portion of leg 234 near the ankle. Irrigation fluid is introduced from irrigation fluid supply 237 into vein 232 through one of the incisions 230 or 236 (or alternatively through a nearby ancillary incision (not shown)) to flush all blood out of vein 232 through the other of the incisions 230 or 236. An actuator 241 is provided to permit the surgeon to actuate irrigation fluid supply 237 periodically. For example, a foot pedal-actuated device (not shown) can be used as an actuator 241 to permit the surgeon to irrigate vein 232 and its side branches prior to and/or after embolization. Blood typically oozes into vein 232 and the surgeon must clear the vein using the irrigation fluid during embolization. A waste irrigation fluid reservoir 239 can be provided to collect waste irrigation fluid passed through the body.

Guide catheter 196 is inserted into vein 232 through first incision 230 and moved therein so that an angioscope 220 deployed in guide catheter 196 can be used to observe each of the randomly spaced one-way check valves 238 situated in vein 232. Typically, four to six of these check valves 238 are formed in the length of saphenous vein 232 used to perform bypass grafts in a human leg. These one-way check valves 238 are configured to allow blood to flow through vein 232 in a direction toward the heart and prevent blood flow in the opposite direction. Initially, the angioscope 220 is moved through vein 232 using guide catheter 196 to a position allowing the surgeon to observe the check valve 238 farthest from the foot.

An apparatus 240 known as a valvulotome is then inserted into the vein 232 through the second incision 236 and advanced therein in a direction away from the foot to contact the one-way check valve 238 observed using the angioscope 220. This apparatus 240 can be used in the conventional way to render each check valve 238 in vein 232 incompetent so that fluid can now flow through vein 232 in either direction. Essentially, this apparatus 240 is used to cut and disable each of the check valves 238 in sequence while the valves 238 are being observed using the angioscope 220 deployed in guide catheter 196.

As shown in FIG. 12, apparatus 240 and angioscope 220 have already cooperated to disable the check valve 238a in vein 232 that is farthest from the foot and have now moved to a position already to cut and disable the next check valve 238b. Check valve 238c has not yet been disabled.

Next, the guide catheter 196 and introducer catheter 16 are used in the manner described above to occlude in sequence each of the side branches (collateral vessels) 242 of vein 232. The vein 232 is then connected to the adjacent occluded or otherwise disabled artery 244 at the top of the artery (through first incision 230) and at the bottom of the artery (through second incision 236) to cause blood to flow through vein 232 instead of through the occluded or diseased segment of the artery 244 so that the vein 232 is transformed into a new artery. The angioscope 220 in guide catheter 196 can be used to inspect the transformed vein 232 to ensure that it will function properly as an artery in its reconfigured state.

Advantageously, the embolus delivery system 10, 190, or 290 can be used to assist in reconfiguring a vein to function as an artery after making only two small incisions in the leg to be treated It will be appreciated that vein reconfiguration surgery using embolus delivery system 10, 190, or 290 is much less invasive than many known surgical procedures which require a long incision to be made along the length of the leg and each side branch of the exposed vein to be ligated by hand. It will be appreciated that the human body has in place multiple collateral veins in the leg, both functional and non-functional, which will automatically become functional and compensate the vein.

Although the invention has been described and defined in detail with reference to certain preferred embodiments, variations and modifications exist within the scope and spirit of the invention as described and defined in the following claims.

What is claimed is:

1. An apparatus for supplying an embolus to a delivery tube, the apparatus comprising
   a magazine containing a plurality of emboli,
   means for moving the magazine relative to the delivery tube to place a selected one of the emboli in the magazine in communication with the delivery tube, and
   means for discharging said selected one of the emboli from the magazine into the delivery tube.

2. The apparatus of claim 1, wherein the moving means includes means for using a stream of pressurized fluid to advance the magazine in a direction toward the delivery tube.

3. The apparatus of claim 2, wherein the using means includes cylinder means for receiving a stream of pressurized fluid and piston means in the cylinder means for advancing the magazine to couple with the delivery tube in response to input of fluid having a pressure in excess of a predetermined pressure into the cylinder means so that the selected one of the emboli in the magazine can be discharged into the delivery tube.

4. The apparatus of claim 1, wherein the moving means includes means for using a stream of pressurized fluid to advance the magazine incrementally in a predetermined indexed manner relative to the delivery tube so that each embolus in the magazine is moved therewith according to a predetermined sequence to an embolus-discharging position communicating with the delivery tube and the embolus in the embolus-discharging position can be discharged into the delivery tube by the discharging means.

5. The apparatus of claim 4, wherein the moving means includes cylinder means for receiving a stream of pressurized fluid, linkage means for advancing the magazine along a path relative to the delivery tube, and piston means for operating the linkage means to advance the magazine incrementally along its path in response to input of fluid having a pressure in excess of a predetermined pressure into the cylinder means.

6. The apparatus of claim 1, wherein the moving means includes a hollow housing containing the magazine, means for guiding the magazine as it moves within the hollow housing to place each selected one of the emboli in communication with the delivery tube, a linkage coupled to the hollow housing and to the magazine, and means for actuating the linkage to move the magazine within the hollow housing to place sequentially each embolus in the magazine in communication with the delivery tube.

7. The apparatus of claim 6, wherein the hollow housing includes an interior wall, the magazine is formed to include a guide slot, and the guiding means includes at least one guide rail appended to the interior wall and configured to extend into the guide slot of the magazine and define a path along which the magazine is capable of traveling through the hollow housing under the control of the moving means.

8. An apparatus for supplying an embolus to a delivery tube, the apparatus comprising
   a magazine containing a plurality of hollow cartridges, each cartridge containing an embolus therein and including outlet means for communicating with the delivery tube,
   means for moving the magazine relative to the delivery tube to place a selected one of the cartridges in the magazine in communication with the delivery tube, and
   means for discharging the embolus in the selected one of the cartridges from the magazine into the delivery tube, each cartridge further including inlet means for communicating with the discharging means.

9. The apparatus of claim 8, wherein the discharging means includes means for conducting a stream of pressurized fluid at a predetermined velocity into the selected cartridge in the magazine through the inlet means of the selected cartridge to discharge the embolus contained therein from the cartridge into the delivery tube through the outlet means of the selected cartridge.

10. The apparatus of claim 9, wherein the moving means includes means for using said stream of pressurized fluid to advance the magazine in a direction toward the delivery tube to cause the outlet means of the selected cartridge to communicate with the delivery tube so that the stream of pressurized fluid can flow from the selected cartridge into the delivery tube through the outlet means.

11. The apparatus of claim 9, wherein the moving means includes means for using said stream of pressurized fluid to advance the magazine incrementally in a predetermined indexed manner relative to the delivery tube so that each cartridge is moved to an embolus-discharging position communicating with the delivery tube according to a predetermined sequence.

12. The apparatus of claim 8, wherein the magazine is formed to include a series of elongated, open-ended magazine chambers extending therethrough, a cartridge is disposed in each magazine chamber to position its inlet means in a first opening of the magazine chamber and its outlet means in a second opening of the magazine chamber, and the moving means includes means for sequentially coupling each magazine chamber in the series to both of the discharging means and the delivery tube to place the inlet means of a cartridge situated in a selected magazine chamber in communication with the discharging means and the outlet means of the cartridge situated in the selected magazine chamber in communication with the delivery tube.

13. The apparatus of claim 12, wherein the discharging means includes means for conducting a stream of pressurized fluid into the selected magazine chamber after the inlet means of the cartridge in the selected magazine chamber is coupled to the discharging means and the outlet means of the cartridge in the selected magazine chamber is coupled to the delivery tube to discharge the embolus contained in the cartridge in the selected magazine chamber from the cartridge into the delivery tube.

14. An apparatus for supplying an embolus to a delivery tube, the apparatus comprising
   a magazine containing a plurality of emboli,
   means for moving the magazine relative to the delivery tube to place a selected one of the emboli in the magazine in communication with the delivery tube, and
   means for discharging said selected one of the emboli from the magazine into the delivery tube, the moving means including a hollow housing containing the magazine, means for guiding the magazine as it moves within the hollow housing to place each selected one of the emboli in communication with the delivery tube, and means for using a stream of pressurized fluid to move the magazine within the hollow housing to place each embolus in the magazine sequentially in communication with the delivery tube so that each embolus can be discharged into the delivery tube one at a time by the discharging means.

15. The apparatus of claim 14, wherein the guiding means includes at least one rail situated within the hollow housing and means for yieldably biasing the magazine into slidable engagement with the at least one rail.

16. The apparatus of claim 15, wherein the using means includes means for slidably advancing the magazine within the hollow housing in a first direction along the at least one rail, cylinder means for receiving the stream of pressurized fluid therein, and piston means for using pressurized fluid received in the cylinder means to move the advancing means relative to the magazine so that the magazine advances along the at least one rail in the first direction while it is biased against said at least one rail by the biasing means.

17. The apparatus of claim 16, wherein the magazine contains a plurality of hollow cartridges, each hollow cartridge is formed to include inlet means for communicating with the discharging means and outlet means for communicating with the delivery tube, each hollow cartridge contains an embolus, and the discharging means includes means extending through an aperture formed in the piston means for conducting the stream of pressurized fluid received in the cylinder means into a selected hollow cartridge in the magazine through the inlet means of the selected hollow cartridge to discharge the embolus contained therein into the delivery tube through the outlet means of the selected hollow cartridge.

18. The apparatus of claim 15, wherein the using means includes drive means for moving the magazine away from the at least one guide rail against a biasing force provided by the biasing means, cylinder means for receiving the stream of pressurized fluid therein, and piston means for using pressurized fluid received in the cylinder means to move the drive means into engagement with the magazine so that the magazine moves away from the at least one rail.

19. The apparatus of claim 18, wherein the magazine contains a plurality of hollow cartridges, each hollow cartridge is formed to include inlet means for communicating with the discharging means and outlet means for communicating with the delivery tube, each hollow cartridge contains an embolus, and the discharging means includes means extending through apertures formed in the piston means and drive means for conducting the stream of pressurized fluid received in the cylinder means into a selected hollow cartridge in the magazine through the inlet means of the selected hollow cartridge to discharge the embolus contained therein into the delivery tube through the outlet means of the selected hollow cartridge 20. An apparatus for supplying an embolus to a delivery tube, the apparatus comprising a hollow housing formed to include an inlet and outlet, a magazine containing a plurality of spaced-apart embolus cartridges arranged in a series, each embolus cartridge being formed to include a passageway extending therethrough and containing an embolus therein, means for moving the magazine inside the housing to align each embolus cartridge in the series in sequence one at a time in an embolus-discharging position within the housing so that the passageway of the embolus cartridge situated in the embolus-discharging position interconnects the housing inlet and outlet, and means for discharging the embolus contained in the passageway of the embolus cartridge situated in the embolus-discharging position from the embolus cartridge through the housing outlet so that the embolus is supplied to the delivery tube connected to the housing outlet.

21. The apparatus of claim 20, wherein the moving means includes means for generating a stream of pressurized fluid and means for using the stream of pressurized fluid to move the magazine inside the housing to align each embolus cartridge in the series in sequence one at a time in the embolus-discharging position within the housing 22. The apparatus of claim 20, wherein the discharging means includes means for generating a stream of pressurized fluid and means for conducting the stream of pressurized fluid into the passageway of the embolus cartridge situated in the embolus-discharging position within the housing so that the embolus in the passageway is discharged into the delivery tube connected to the housing outlet along with the stream of pressurized fluid.

23. The apparatus of claim 20, wherein the moving means includes cylinder means for receiving a stream of pressurized fluid and a piston disposed in the cylinder means for movement therein.

24. The apparatus of claim 23, wherein the moving means further includes spring return means for yieldably biasing the piston to a first position in the cylinder means, the piston is configured to move to a second position in the cylinder means upon input of the stream of pressurized fluid into the cylinder means, the magazine is formed to include a serpentine groove, and the piston includes a drive bar extending into the hollow housing and pawl means coupled to the drive bar for riding in the serpentine groove in response to movement of the piston between its first and second position in the cylinder means so that the magazine moves a first incremental distance in a first direction with respect to the hollow housing in response to movement of the piston from its first position to it second position and a second incremental distance in said first direction with respect to the hollow housing in response to movement of the piston from its second position to its first position.

25. The apparatus of claim 23, wherein the piston is formed to include an aperture extending therethrough and the discharging means includes means extending through the aperture formed in the piston means for conducting the stream of pressurized fluid from the cylinder means into the passageway of the embolus cartridge situated in the embolus-discharging position and means for sealingly coupling said passageway to the housing outlet so that the embolus and the stream of pressurized fluid in said passageway are discharged simultaneously from the magazine into the delivery tube.

26. The apparatus of claim 25, wherein the conducting means includes a fluid-conducting conduit coupled to the piston aperture, a valve movable in the conduit between aperture-opening and aperture-closing positions, and means for yieldably biasing the valve to its aperture-closing position to block flow of pressurized fluid from the cylinder means into the passageway in the embolus cartridge until the pressure of fluid in the cylinder means exceeds a predetermined threshold level and the passageway in the embolus cartridge situated in the embolus-discharging position is coupled to the delivery tube through the housing outlet.

27. The apparatus of claim 20, wherein the moving means includes means for guiding the magazine along a guide path passing through the embolus-discharging position and means for using a stream of pressurized fluid to move the magazine within the hollow housing to place each embolus cartridge one at a time in the embolus-discharging position 28. The apparatus of claim 27, wherein the discharging means includes means for conducting said stream of pressurized fluid into the passageway formed in the embolus cartridge placed in the embolus-discharging position to discharge the embolus contained therein into the delivery tube.

29. An apparatus for supplying an embolus to a delivery tube, the apparatus comprising
a magazine containing a plurality of embolus cartridges arranged in a series, each embolus cartridge being formed to include a fluid-conducting passageway extending therethrough,
a hollow housing providing an embolus-discharge station therein and including a housing inlet and outlet and means for guiding the magazine along a guide path intersecting the embolus-discharge station as the magazine moves inside the hollow housing, the housing outlet providing means for connecting to the delivery tube,
means for passing a stream of pressurized fluid through the housing inlet into the fluid-conducting passageway in an embolus cartridge temporarily positioned to lie in the embolus-discharge station in communication with both of the housing inlet and outlet so that an embolus provided in the fluid-conducting passageway of the embolus cartridge is discharged through the housing outlet into the delivery tube at least at a predetermined velocity to empty the embolus cartridge positioned in the embolus-discharge station, and
means for moving the magazine within the hollow housing along the guide path a predetermined distance to move a just-emptied embolus cartridge out of the embolus-discharge station and a next embolus cartridge in the series of embolus cartridges into the embolus-discharge station to lie in communication with both of the housing inlet and outlet ready to receive the stream of pressurized fluid provided by the passing means.

30. The apparatus of claim 29, wherein the moving means includes cylinder means for receiving the stream of pressurized fluid, linkage means for advancing the magazine along the guide path, and piston means for operating the linkage means to advance the magazine along the guide path in response to input of fluid having a pressure in excess of a predetermined pressure into the cylinder means.

31. The apparatus of claim 30, wherein the passing means includes means for conducting the stream of pressurized fluid through a conduit from the cylinder means into the passageway of the embolus cartridge situated in the embolus-discharge station, a valve movable in the conducting means between a conduit-opening and conduit-closing positions, and means for yieldably biasing the valve to its conduit-closing position to block flow of pressurized fluid from the cylinder means into the passageway of the embolus cartridge situated in the embolus-discharge station until the pressure of fluid in the cylinder means exceeds a predetermined threshold level.

32. A method of delivering an embolus to a destination, the method comprising the steps of
inserting a catheter into a body, the catheter being formed to include an inlet, an outlet, and a lumen connecting the inlet to the outlet,
guiding the catheter through the body to aim the outlet of the catheter toward the destination,
connecting a device containing a plurality of emboli to the inlet of the catheter,
providing a stream of pressurized fluid, and
using the stream of pressurized fluid to flush one embolus at a time out of the device and move the flushed embolus into and through the lumen to reach the destination.

33. The method of claim 32, wherein the using step includes the steps of aiming the stream of pressurized fluid at said one embolus and conducting said one embolus and the stream of pressurized fluid into the lumen through the inlet formed in the catheter.

34. The method of claim 32, wherein the using step further includes the steps of providing a supply of fluid and pressurizing fluid from the supply at a predetermined rate to generate the stream of pressurized fluid.

35. The method of claim 32, wherein the using step includes the step of introducing the stream of pressurized fluid into the device for a predetermined length of time through an inlet port formed in the device to discharge said one embolus from the device through an outlet port formed in the device into the inlet of the catheter.

36. The method of claim 32, wherein the providing step includes the step of connecting a syringe means having a body filled with fluid to an inlet port formed in the device and moving a plunger in the body to discharge a stream of pressurized fluid from the syringe means into the device through the inlet port.

37. The method of claim 32, wherein the embolus is a coiled spring uncoiled to assume a straightened, packed position in the hollow cartridge and configured to exert a predetermined force against an interior wall of the device to retain the embolus in an initial position within the hollow cartridge, and the providing step includes the steps of supplying a liquid and pressurizing the liquid at a predetermined rate to generate the stream of pressurized fluid and provide a predetermined amount of work needed to overcome frictional forces between said one embolus and the interior wall of the device.

38. The method of claim 32, wherein the guiding step includes the step of conducting the outer catheter through a vein in a body an inserting the outer catheter into a side branch of the vein to position the outlet of the outer catheter in the side branch, the moving step includes the step of positioning the embolus-discharging outlet of the inner catheter in the side branch of the vein, and said one embolus is flushed out of the inner catheter and into the side branch to occlude the side branch during the using step.

39. A method of delivering an embolus to a selected destination, the method comprising the steps of inserting an outer catheter into a body, the outer catheter being formed to include a lumen having an inlet and an outlet, guiding the outer catheter through the body to aim the outlet of the lumen at the selected destination, inserting an inner catheter into the lumen of the outer catheter, the inner catheter being formed to include an embolus-conducting lumen having an embolus-admitting inlet and an embolus-discharging outlet, moving the inner catheter in the lumen of the outer catheter to project the embolus-discharging outlet through the outlet of the outer catheter so that an embolus discharged from the embolus-conducting lumen is deposited at the selected destination, connecting a device containing a plurality of emboli to the embolus-admitting inlet of the inner catheter, and using a fluid to flush one embolus at a time out of the device and move the flushed embolus into and through the embolus-conducting lumen to reach the selected destination.

40. The method of claim 39, wherein the using step further includes the steps of providing a supply of fluid and pressurizing a predetermined volume of fluid from the supply at a predetermined rate to generate the stream of pressurized fluid.

41. The method of claim 39, wherein the connecting step further includes the steps of providing a device containing a plurality of hollow cartridges, each hollow cartridge being formed to include a passageway containing an embolus lodged temporarily therein in frictional engagement with a wall defining the passageway and moving the hollow cartridges within the device to connect the passageway of one of the hollow cartridges at a time to the lumen of the catheter to permit the movement of an embolus therebetween through the inlet, and the using step further includes the steps of providing a supply of fluid, pressurizing a predetermined volume of fluid from the supply at a predetermined rate to generate the stream of pressurized fluid, and aiming the stream of pressurized fluid to apply a predetermined amount of work to the embolus in said one of the hollow cartridges to overcome frictional forces between the embolus and the wall of the passageway and dislodge the embolus during the using step.

42. The method of claim 41, wherein the connecting step further includes the steps of providing a spring having a coiled shape to serve as the embolus, uncoiling the spring to cause it to move to assume a straightened shape, and packing the spring of straightened shape into the passageway, which passageway is sized to block the spring from reforming to its shape so that the spring is lodged temporarily in a fixed position in the passageway by frictional engagement of the spring and a wall defining the passageway and the using step includes the steps of providing a supply of fluid, pressurizing a predetermined volume of fluid from the supply at a predetermined rate to generate the stream of pressurized fluid, and employing the stream of pressurized fluid to apply a predetermined amount of work to the spring to overcome frictional forces between the spring and the wall of the passageway and propel the spring from its fixed position in the passageway through the lumen of the catheter so that the spring exits the outlet and reforms to assume its coiled shape at the destination.

43. A method of delivery an embolus to a destination, the method comprising the steps of inserting a catheter into a body, the catheter being formed to include an inlet, an outlet, and a lumen connecting the inlet to the outlet, guiding the catheter through the body to aim the outlet of the catheter toward the destination, connecting a device containing a plurality of emboli to the inlet of the catheter, and discharging one embolus at a time out of the device into and through the lumen of the catheter to reach the destination.

44. The method of claim 43, wherein the discharging step includes the step of injecting pressurized fluid into the device through an inlet formed in the device.

45. The method of claim 44, wherein the discharging step further includes the steps of positioning a single embolus in a predetermined position in the device and confining the pressurized fluid introduced into the device during the injecting step to impact said single embolus and carry it out of the device through an outlet formed in the device into the lumen of the catheter.

46. The method of claim 43, wherein the discharging step includes the step of using a guide wire to move each embolus out of the device into and through the lumen of the catheter.

47. The method of claim 43, wherein the discharging step includes the steps of connecting a syringe means having a body filled with fluid to an inlet formed in the device and operating the syringe means to discharge pressurized fluid from the body into the device through an inlet formed in the device.

48. The method of claim 47, wherein the discharging step further includes the steps of positioning a single embolus in a predetermined position in the device and confining the pressurized fluid introduced into the device during the operating step to impact said single embolus and carry it out of the device through an outlet formed in the device into the lumen of the catheter.

* * * * *